(12) United States Patent
Meir et al.

(10) Patent No.: US 8,662,083 B2
(45) Date of Patent: Mar. 4, 2014

(54) BLANK FOR A HEAD RESTRAINT

(75) Inventors: Ivan D Meir, London (GB); James O Turner, London (GB)

(73) Assignee: Vision RT Limited, London (GB)

( * ) Notice: Subject to any disclaimer, the term of this patent is extended or adjusted under 35 U.S.C. 154(b) by 163 days.

(21) Appl. No.: 13/145,667

(22) PCT Filed: Jan. 22, 2010

(86) PCT No.: PCT/GB2010/050095
§ 371 (c)(1),
(2), (4) Date: Sep. 27, 2011

(87) PCT Pub. No.: WO2010/084354
PCT Pub. Date: Jul. 29, 2010

(65) Prior Publication Data
US 2012/0006336 A1     Jan. 12, 2012

(30) Foreign Application Priority Data
Jan. 26, 2009   (GB) .................................. 0901220.4

(51) Int. Cl.
*A61F 11/00*     (2006.01)
(52) U.S. Cl.
USPC ............................. 128/857; 128/869; 128/870
(58) Field of Classification Search
USPC ............... 128/857, 869–870; 606/130; 5/601, 5/621–622, 637; 378/20, 68, 177, 195, 378/208
See application file for complete search history.

(56) References Cited

U.S. PATENT DOCUMENTS

| | | | |
|---|---|---|---|
| 5,370,117 A | 12/1994 | McLaurin, Jr. | |
| 6,138,302 A | 10/2000 | Sashin et al. | |
| 2002/0038659 A1 | 4/2002 | Al-Kassim | |
| 2005/0229936 A1 | 10/2005 | Ungemach et al. | |
| 2005/0284490 A1 | 12/2005 | Moyers | |
| 2006/0053556 A1 | 3/2006 | Piontek | |

FOREIGN PATENT DOCUMENTS

WO    WO 03/061477 A1    7/2003

OTHER PUBLICATIONS

Aug. 4, 2011 Written Opinion issued in International Application No. PCT/GB2010/050095.

*Primary Examiner* — Patricia Bianco
*Assistant Examiner* — Camtu Nguyen
(74) *Attorney, Agent, or Firm* — Oliff PLC

(57) ABSTRACT

A blank for a head restraint is disclosed. The blank includes a frame and a sheet extending across the frame wherein a main aperture and a pair of auxiliary apertures are provided in the sheet. The arrangement of the apertures is such that when the sheet is deformed upon placement on a patient's head, the main aperture is such to leave a patient's face substantially free of the sheet and the auxiliary apertures are such to cause a retaining strut to be formed by portions of the sheet between the main aperture and the auxiliary apertures.

11 Claims, 2 Drawing Sheets

BLANK FOR A HEAD RESTRAINT

FIELD OF THE INVENTION

Figure 1:
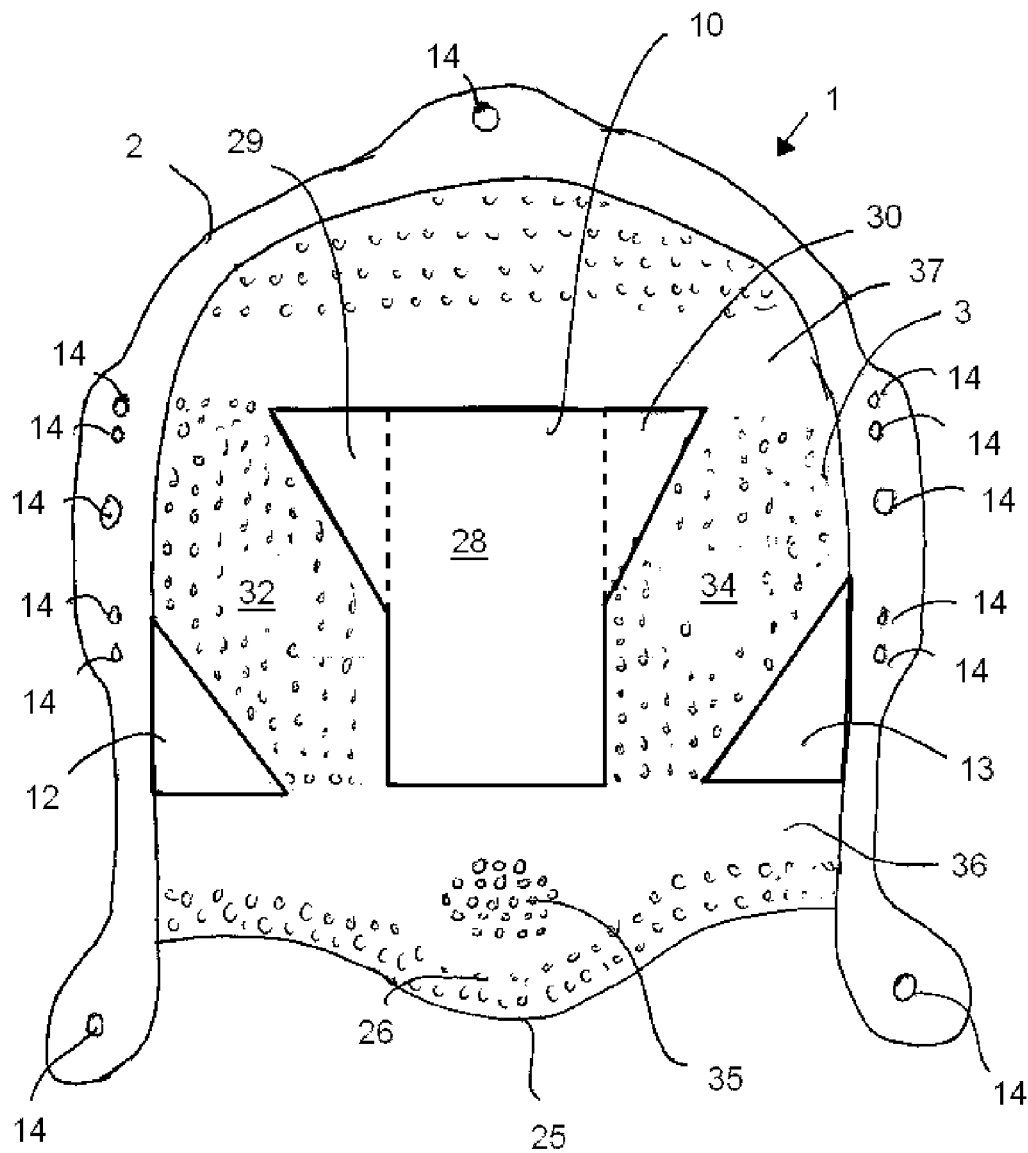

The present invention concerns a patient immobilisation assembly for restraining a patient's head. In particular, embodiments of the present invention concern devices for immobilising the head and neck of a patient during radiotherapy.

BACKGROUND TO THE INVENTION

Radiotherapy is a form of cancer treatment which involves the application of radiation directed to a particular situs in a patient's body. The applied radiation destroys targeted cancer cells. However, the radiation can also affect some of the normal cells nearby. Where the radiotherapy is used to treat cancers of the head and neck, the destruction and damage of nearby healthy tissue can result in severe side effects due to the presence of many critical structures and organs in that part of the body. For this reason, it is very important that radiation is targeted as far as possible so as to destroy only the cancerous cells whilst leaving other nearby structures intact.

Devices immobilising the position of a patient's head and neck are used to improve the accuracy and reproducibility of positioning the head and neck in medical diagnostic and treatment procedures. These devices are particularly important when a patient is undergoing fractionated radiation therapy where radiation is applied to a patient on a number of different occasions. When undergoing fractionated treatment it is important to try to ensure that a patient is placed in the same position for each treatment session so that the same location can be irradiated throughout the course of treatment.

One of the simplest approaches to assist a patient to maintain their position is with use of a chin strap. However, this approach fails to immobilise the head and neck completely which increases the chances of a patient moving during a treatment session and hence the dangers of detrimental side affects. A simple chin strap also fails to ensure that a patient will be positioned consistently during the course of multiple treatment sessions.

To address this problem it is known to immobilise a patient's head using a full-face mask. Such a full-face mask is normally made out of a thermoplastic material which is heated prior to an initial treatment session. The mask is then moulded to a patient's head by being placed over the patient's face and then allowed to set. The resultant full-face mask completely encloses a patient's head and thus restricts movement and allows a patient to be placed into a fixed position for each treatment session. Examples of such full face masks are disclosed in WO03/061477 and WO04/032781.

Although a full-face mask is an improvement on immobilising a patient solely with a chin strap existing masks suffer from a number of drawbacks.

As the mask covers the vast majority or the entirety of a patient's face with only small apertures for eyeholes, some patient's find existing masks claustrophobic and uncomfortable. Further, although the full-mask approach substantially limits a patient's movement as the mask encloses a patient's head, it is still possible for small movements to occur within the mask. Further as the mask completely obscures a patient's face it is not possible to monitor for movement during treatment.

An alternative head restraint for maintaining the position of a patient during a medical procedure such as imaging by position emission tomography (PET) or magnetic resonance imaging (MRI) is disclosed in WO00/27331. WO 00/27331 is an example of a prior art head restraint for use with a tracking system as such the face leaves a portion of the face unobscured. However the design of the mask of WO 00/27331 suffers from similar problems to the chinstrap prior art.

An alternative immobilisation assembly that assists with precise positioning of the patient's head during repeated and subsequent treatments and examinations whilst increasing a patient's comfort is therefore desirable.

SUMMARY OF THE INVENTION

In accordance with one aspect of the present invention there is provided a blank for a head restraint comprising: a frame; and a sheet extending across the frame wherein a main aperture and a pair of auxiliary apertures are provided in the sheet, the arrangement of the apertures being such that when the sheet is deformed upon placement on a patient's head the main aperture is such to leave a patient's face substantially free of the sheet and the auxiliary apertures are such to cause a retaining strut to be formed by portions of the sheet between said main aperture and said auxiliary apertures.

BREIF DESCRIPTION OF THE DRAWINGS

Figure 2:
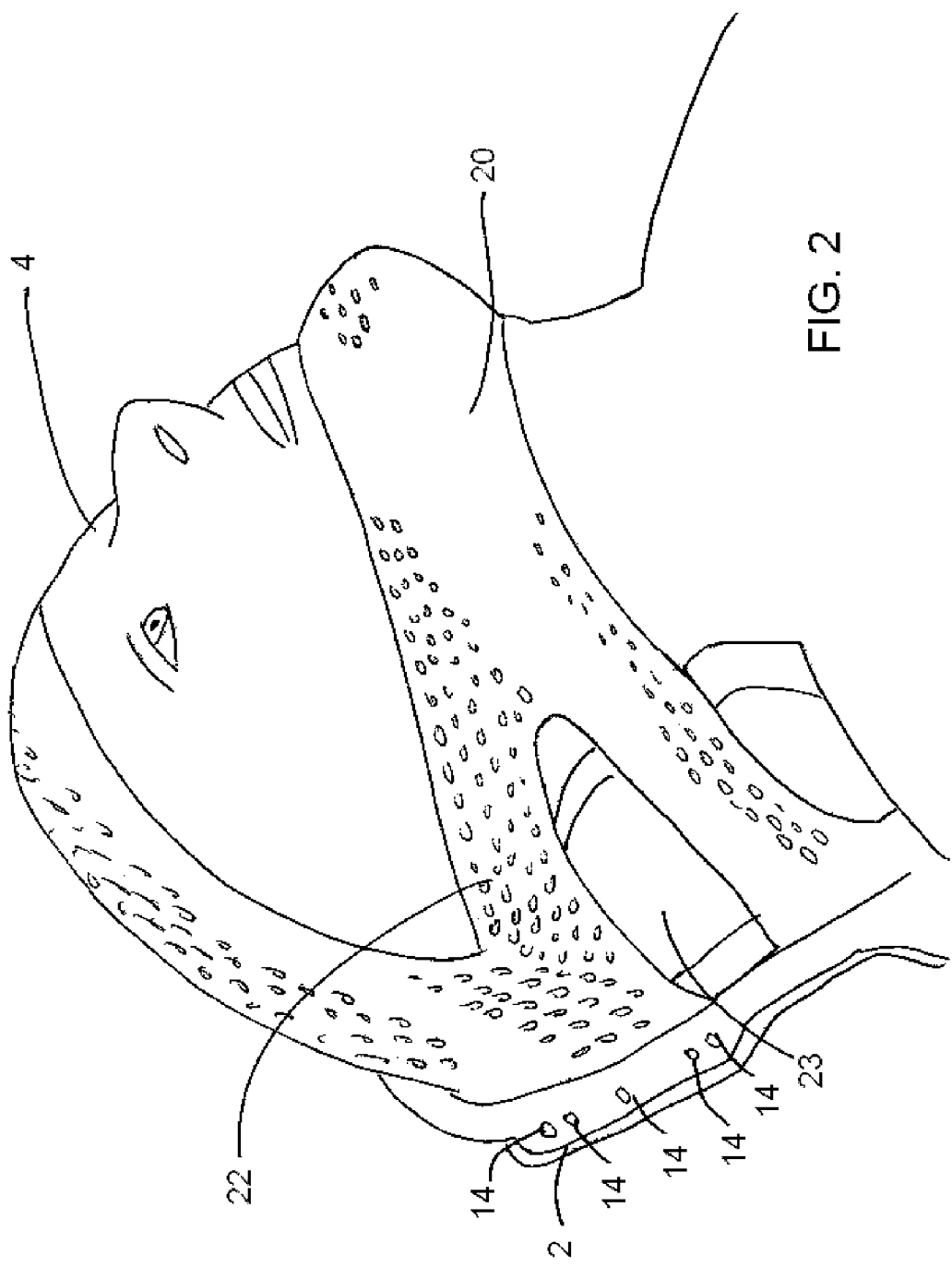

Further aspects and embodiments of the present invention will become apparent with reference to the following description and accompanying drawings in which:

FIG. 1 is a frontal view of a blank for an immobilising head restraint in accordance with an embodiment of the present invention; and FIG. 2 is a perspective view of the head and neck of a patient wearing a head restraint formed from the blank of FIG. 1.

DETAILED DESCRIPTION OF THE PREFERRED EMBODIMENT

FIG. 1 is a front view of a head restraint blank 1 in accordance with a first embodiment of the present invention. The blank 1 is also illustrated in FIG. 2 which comprises a schematic perspective view of the head restraint blank 1 after deformation by a patient's head 4.

Referring to FIG. 1, the blank head restraint 1 comprises a rigid U-shaped frame 2 with an integrally formed perforated sheet 3. The perforated sheet 3 is made from a thermoplastic which when heated can be deformed by being placed over a patient's head. In this embodiment the perforated sheet has three large apertures comprising a main central aperture 10 and two subsidiary triangular apertures 12, 13 provided either side of the main central aperture 10. A series of screw holes 14 are provided in the frame 2 enabling the frame 2 to be attached to a restraint platform.

As is illustrated in FIG. 2, the arrangement of the apertures 10, 12, 13 in the perforated sheet 3 is such that when the blank 1 is deformed by being placed over a patient's face, the perforated sheet 3 is moulded and stretched to sculpt the contours of the patient's head whilst leaving the patient's face, including eyes, nose and mouth, to be uncovered. At the same time the portions of the perforated sheet 3 between the apertures 10, 12, 13 are stretched so as to form a chin strap 20 and a pair of accompanying side struts 22 either side of the patient's face which together act to restrain the patient's head 4 in place whilst giving the deformed sheet 3 substantial structural rigidity thus ensuring that despite the fact that the patient's face is unenclosed, the mask acts to retain the patient's head 4 in a fixed position when it lies on a cushion 23 provided as part of a restraint platform. In addition to being more comfortable for a patient, leaving the patient's face uncovered enables movement of the patient to be detected using non-contact motion detection systems such as Vision RT's AlignRT® system such as is disclosed in WO2004/004828.

Returning to FIG. 1, before being deformed the perforated sheet 3 substantially fills the entirety of the U-shaped frame 2 with the edge 25 of the perforated sheet 3 at the open end of the U-shaped frame 2 following a serpentine curve initially running approximately perpendicularly to the arms of the frame 2 before moving away from the apex of the U-shaped frame 2 so as to provide a small additional protrusion 26 in the central portion of the sheet 3. As is shown in FIG. 2 this protrusion 26 is such to enable the portion of the perforated sheet 3 to form a chin strap 20 which encloses a patient's chin when the blank 1 has been deformed.

In this embodiment, the main central aperture 10 comprises a central rectangular portion 28 and two adjacent wing portions 29, 30 where, the central rectangular portion 28 extends across the middle third of the perforated sheet 3 with the longer sides of the central rectangular portion 28 running parallel with the arms of the U-shaped frame 2. The two wing portions 29, 30 each comprise right angled triangular openings each with bases extending half way down the long sides of the central rectangular portion 28 and with each two wing portion 29, 30 having an apex level with the edge 25 of the central rectangular portion 28 remote from the edge 25 of the perforated sheet 3 half way between the long side of the central rectangular portion 28 and the edge 25 of the U-shape frame 2.

In this embodiment in order to increase the resistance of some areas of the perforated sheet 3 to deformation some areas of the sheet 3 are left free of perforations. More specifically, other than in a central area 35 of the section of the sheet 3 and a band 36 immediately adjacent to the open end of the U-shaped frame 2, the portion of the sheet 3 adjacent to the open end of the U-shaped frame 2 is left free from perforations. In use this causes the central area 35 and the section of sheet 3 immediately adjacent to the open end of the U-shaped frame 2 to deform more easily and so accommodate the shape of a patient's chin. Also a band 37 of sheet 3 running across the edge of the main aperture 10 remote from the open end of the U-shaped frame 3 extending across to the arms of the frame 2 is also left free from perforations.

The two subsidiary triangular apertures 12, 13 each comprise a right-angled triangular opening. The two subsidiary triangular apertures 12, 13 lie either side of the main central aperture 10 with a base adjacent to the arms of the U-shaped frame 2 and apex level with the end of the edge of the central rectangular portion 28 of the main central aperture 10 with the hypotenuses of the winged portions 29, 30 of the main aperture 10 and the triangular apertures 12, 13 being parallel to each other.

In this way, the edges of main aperture 10 and the two subsidiary triangular apertures 12, 13 define the edges of a pair of strips 32, 34 of the perforated sheet 3 lying either side of the main aperture 10 connecting the U-shaped frame 2 with the portion of the sheet 3 adjacent to the open end of the U-shaped frame 2. In use as is shown in FIG. 2, these strips 32, 34 are deformed so as to form the struts 22 connecting the chin strap 20 formed from the portion of the sheet 3 adjacent to the open end of the U-shaped frame 2 with a portion of the U-shaped frame 2 further from the open end of the frame 2.

Once set after being deformed the perforated sheet 3 will resist further deformation when placed under tension. In use the lower portion of the deformed sheet 3 acts to retain a patient's head 4 in position as this portion of the sheet 3 forms a chin strap 20 which prevents movement of a patient's chin away from the plane of the U-shaped frame 2. Similarly, the portion of the perforated sheet 3 remote from the open end of the U-shaped frame 2 prevents forehead of a patient 4 from being moved away the plane of the U-shaped frame 2. Finally, the portion of the perforated sheet 3 remote from the open end of the U-shaped frame 2 and the struts 22 formed from the strips 32, 34 between the main central aperture 10 and the two subsidiary apertures 12, 13 together prevent movement the direction parallel with the arms of the U-shaped frame 2.

In particular, it will be noted that by providing the two subsidiary apertures 12, 13 and the main central aperture 10 in the manner described above movement a head restraint is formed which resists motion but which has an opening which leaves a patient's face uncovered is formed. This is because the orientation of the struts 22 formed from the strips 32, 34 between the main central aperture 10 and the two subsidiary apertures 12, 13 are such to be placed under tension by any movement towards the open end of the U-shaped frame 2 and thus provide the head restraint with structural rigidity under tension even in the absence of the perforated sheet 3 covering the face of the patient.

Further Modifications and Embodiments

Although in the above described embodiment the main aperture 10 consists of a central rectangular portion 28 and two adjacent wing portions 29, 30, it will be appreciated that the present invention is not limited to this arrangement and a main aperture 10 may have alternative configurations. Thus for example, embodiments could be provided where the main aperture lacks winged portions 29, 30. Alternatively the main aperture could be triangular or in the form of a parallel trapezium. Additionally rather than having straight sides any or all the edges of the main aperture 10 could be curved.

Although in the above described embodiment, the wing portions 29, 30 of the main central aperture 10 parallel to the two subsidiary apertures 12, 13, it will be appreciated that the present invention is not limited to these apertures being triangles as illustrated in FIGS. 1 and 2 and similar arrangements could be provided where the wing portions 29, 30 and two subsidiary apertures 12, 13 comprise of a enclosed apertures with two concave sides.

It will be appreciated that preferably the edges of the main aperture 10 and the subsidiary apertures 13 should be approximately parallel to each other to assist in the formation of a suitable retaining strut 22.

Although in the above described embodiment, use of bands free from perforation have been limited to two parallel bands, it will be appreciated that the present invention could contain more bands free from perforation in the portion remote from the open end of the U-shaped frame 2 such that the bands extend from the middle of band of free from perforations in a radially symmetrical manner.

In some embodiments, the perforated sheet 3 may have perforations of different sizes. In such embodiments the arrangement of perforations should be such that large perforations are provided in portions of the sheet 3 which are required to under go greater amounts of deformation.

The invention claimed is:
1. A blank for a head restraint comprising:
a frame having an open end; and
a deformable sheet extending across the frame, the sheet defining a main aperture at a central portion within the frame, and a pair of auxiliary apertures on either side of the main aperture adjacent the open end of the frame,
the main and auxiliary apertures being configured such that when the sheet is deformed upon placement on a patient's head within the frame:

1) a portion of the sheet remote from the open end of the frame deforms to enclose the top of the patient's head, and
2) a portion of the sheet adjacent the open end of the frame deforms to define a chin strap enclosing the patient's chin, the main aperture being configured so as to leave the patient's face substantially free of the sheet, and the main and auxiliary apertures being configured so as to define a retaining strut between an attachment point adjacent the frame to the portion of the sheet deformed to become the chin strap enclosing the patient's chin, the retaining strut being formed by portions of the sheet between said main aperture and said auxiliary apertures.

2. The blank of claim 1 wherein said frame comprises a U-shaped frame.

3. The blank of claim 1 wherein the main aperture is triangular or trapezoid in shape.

4. The blank of claim 1 wherein the main aperture comprises a central rectangular portion and a pair of winged sections either side of the central rectangular portion.

5. The blank of claim 4 wherein the auxiliary apertures are substantially triangular in shape.

6. The blank of claim 5 wherein an edge of the main aperture is substantially parallel with an edge of one of the auxiliary apertures.

7. The blank of claim 4 wherein the winged sections either side of the central rectangular portion are substantially triangular in shape.

8. The blank of claim 1 wherein the deformable sheet comprises a thermoplastic material deformable when heated and rigid when cool.

9. The blank of claim 1 wherein the sheet comprises a perforated sheet.

10. The blank of claim 9 wherein the perforations in the sheet are of different sizes.

11. The blank of claim 9 wherein at least some portions of the sheet are substantially free of perforations.

* * * * *